United States Patent [19]

Singer

[11] Patent Number: 5,046,506
[45] Date of Patent: Sep. 10, 1991

[54] MOLDED NEEDLE WITH ADHESIVE

[75] Inventor: Theodore Singer, Northbrook, Ill.

[73] Assignee: Singer Medical Products, Inc., Bensenville, Ill.

[21] Appl. No.: 478,246

[22] Filed: Feb. 9, 1990

[51] Int. Cl.5 .................................. A61H 39/02
[52] U.S. Cl. .................................. 128/741; 606/32
[58] Field of Search ............... 128/741, 642, 784, 802; 606/32

[56] References Cited

U.S. PATENT DOCUMENTS

| | | | |
|---|---|---|---|
| 3,144,018 | 8/1964 | Head | 128/642 |
| 3,830,226 | 8/1974 | Staub et al. | 128/741 |
| 4,962,766 | 10/1990 | Herzon | 128/741 |

Primary Examiner—Lee S. Cohen
Attorney, Agent, or Firm—Hill, Van Santen, Steadman & Simpson

[57] ABSTRACT

An electrical contact surgical needle which has a body member to which the needle is attached and the body member has a planar side which forms an obtuse angle with the needle. Adhesive is located on the planar side and a peel-away cover is mounted over the adhesive.

3 Claims, 1 Drawing Sheet

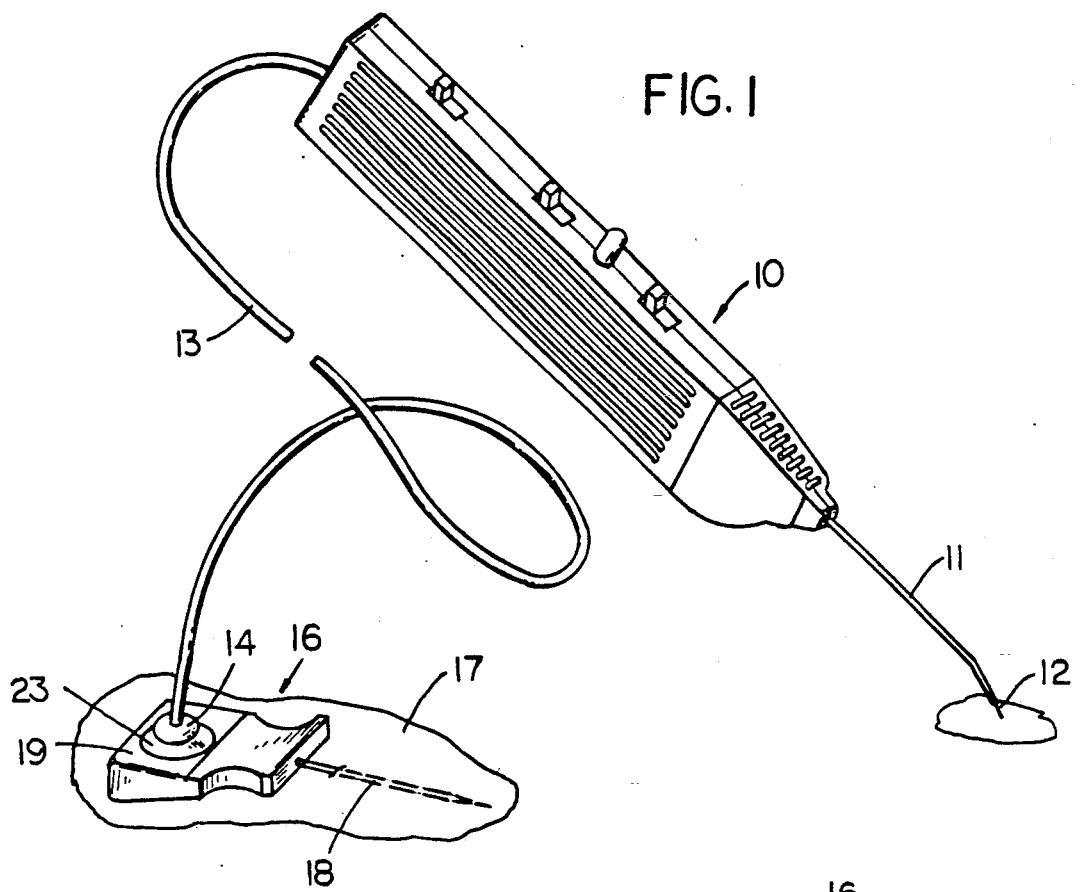
FIG. 1
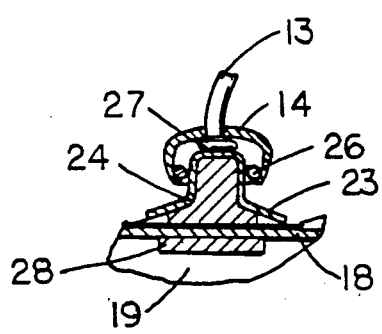
FIG. 2
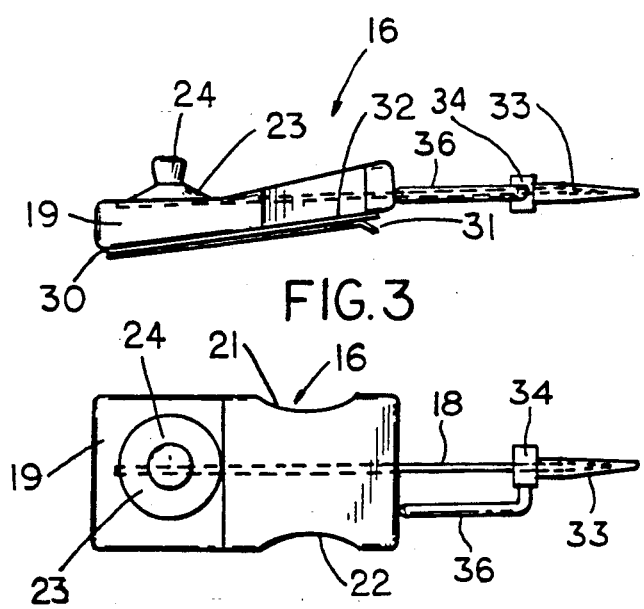
FIG. 3
FIG. 4

MOLDED NEEDLE WITH ADHESIVE

CROSS-REFERENCES TO RELATED APPLICATION

This application is related to application entitled A NERVE LOCATOR IN STIMULATOR, Ser. No. 381,811, filed July 19, 1989 in which the inventor is Garrett D. Herzon assigned to the assignee of the present application.

BACKGROUND OF THE INVENTION

1. Field of the Invention

This invention relates in general to surgical needles and in particular to a molded needle with adhesive which can be attached to a patient.

2. Description of the Related Art

Application Ser. No. 381,811 referenced above discloses a grounding connector for a nerve locator and stimulator which comprises a pad which can be attached to a patient to provide a grounding electrode. Surgeons have indicated that they would like to have the option of providing a ground to the patient with a needle electrode.

SUMMARY OF THE INVENTION

At times it is desirable to provide a grounding needle to a patient during an operation so as to check nerves with a nerve locator or for other purposes.

The present needle electrode includes a holder member and a surgical protective cap over the needle which can be broken away by the surgeon so that the needle can be inserted into the patient. The needle is mounted in a plastic body molded about it which on one side is provided with an adhesive with a peel away cover so that the peel away cover can be removed to attach the plastic body and the needle to the patient. The needle of the invention has an electrical contact which can be connected to a suitable lead for providing an electrical contact to the patient's body.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

BRIEF DESCRIPTION OF THE DRAWINGS

FIG. 1 is a perspective view of the molded needle with adhesive of the invention connected to a nerve stimulator;

FIG. 2 is a sectional view taken on FIG. 1 illustrating the electrical contact;

FIG. 3 is a side plan view illustrating the molded needle with adhesive; and

FIG. 4 is a top plan view illustrating the molded needle with adhesive.

DESCRIPTION OF THE PREFERRED EMBODIMENTS

FIG. 1 illustrates a nerve stimulator 10 such as described in copending application Ser. No. 381,811 filed July 19, 1989 referenced above Which has a body portion and an extending probe 11 with a nerve probe 12. A lead 13 extends from the body member of the nerve stimulator 10 and has a connector 14 which can be detachably connected to a connector 23 of the molded needle with adhesive 16.

The molded needle with adhesive 16 comprises a surgical needle 18 which is embedded in a plastic body member 19 formed with finger depressions 21 and 22. The needle 18 extends through the plastic body portion 19 and is electrically connected to the electrical connection 23 which has an extending prong 24 which is receivable in the mating connector 14 of the nerve stimulator 10 as shown in FIG. 2. A spring 26 is mounted in the connector 14 and passes over the prong 24 as illustrated so that electrical contact is made between the end of prong 24 and a connector pad 27 which connects to the lead 13. The needle 18 is electrically connected to the member 23 by a connector 28 as shown in FIG. 2. The needle 18 can also be welded to the member 23 if desired.

As is best shown in FIGS. 3 and 4, the plastic body member 19 is formed with a planar surface 32 which makes an obtuse angle with the needle 18. Adhesive material 30 is mounted on the planar surface 32 and a peel-away cover 31 is connected over the adhesive 30. A break-away protective molded cap 33 is attached to the plastic body member 19 by an extension 36. A ring 34 is formed in the protective cover 33 so that the protective cover 33 can be easily broken away from the body member 19 and removed from the needle so as to insert the needle into the body 17 of the patient as illustrated in FIG. 1. The peel-away cover 31 is removed and the plastic body member is depressed against the skin of the patient so as to hold the needle 18 in position. Electrical contact 14 can then be attached to the electrical contact 23 and 24 to make electrical contact with the patient's body.

Although the invention has been described with respect to preferred embodiments, it is not to be so limited as changes and modifications can be made which are within the full intended scope of the invention as defined by the appended claims.

I claim as my invention:

1. A grounding medical needle comprising, a body member formed with at least one planar side, an electrically conducting needle attached to said body member and making an obtuse angle with said one planar side, adhesive on said one planar side, a first electrical connector mounted on said body member and in electrical contact with said needle, and a peel away cover on said adhesive on said one planar side which can be removed so as to attach said body member to a patient.

2. A grounding needle according to claim 1 wherein said body member is formed with finger depressions for inserting and attaching said needle to a patient.

3. The combination comprising, a body member formed with at least one planar side, an electrically conducting grounding needle attached to said body member and making an obtuse angle with said one planar side, adhesive on said one planar side, a first electrical connector mounted on said body member and in electrical contract with said needle, a peel away cover on said adhesive on said one planar side which can be removed so as to attach said body member to a patient, and a second electrical connector detachably engaged with said first electrical connector, and an electrical lead connected to said second electrical connector.

* * * * *